(12) United States Patent
Wildeman

(10) Patent No.: US 10,517,778 B2
(45) Date of Patent: Dec. 31, 2019

(54) LOOP FASTENER MATERIAL FOR DIAPER AND RELATED METHOD

(71) Applicant: TIETEX INTERNATIONAL, LTD., Spartanburg, SC (US)

(72) Inventor: Martin Wildeman, Spartanburg, SC (US)

(73) Assignee: TIETEX INTERNATIONAL LTD., Spartanburg, SC (US)

( * ) Notice: Subject to any disclaimer, the term of this patent is extended or adjusted under 35 U.S.C. 154(b) by 952 days.

(21) Appl. No.: 14/628,617

(22) Filed: Feb. 23, 2015

(65) Prior Publication Data

US 2015/0238374 A1 Aug. 27, 2015

Related U.S. Application Data

(60) Provisional application No. 61/944,356, filed on Feb. 25, 2014.

(51) Int. Cl.
  *A61F 13/15* (2006.01)
  *A61F 13/62* (2006.01)
  *A61F 13/56* (2006.01)

(52) U.S. Cl.
  CPC ........ *A61F 13/627* (2013.01); *A61F 13/5633* (2013.01); *A61F 13/5638* (2013.01)

(58) Field of Classification Search
  CPC . A61F 13/5633; A61F 13/5638; A61F 13/627
  USPC .................. 604/391, 387, 394, 396
  See application file for complete search history.

(56) References Cited

U.S. PATENT DOCUMENTS

| | | | |
|---|---|---|---|
| 5,707,707 A | 1/1998 | Burnes et al. | |
| 2004/0115388 A1 | 6/2004 | Wildeman | |
| 2007/0275622 A1 | 11/2007 | Masuda et al. | |
| 2009/0068393 A1 | 3/2009 | Homolle et al. | |
| 2010/0015386 A1* | 1/2010 | Baldauf | A44B 18/0011 428/99 |
| 2011/0028936 A1* | 2/2011 | Wildeman | A61F 13/627 604/391 |
| 2011/0152819 A1 | 6/2011 | Wildeman et al. | |

FOREIGN PATENT DOCUMENTS

WO WO2003/000164 A1 1/2003
WO WO2009/094530 A1 7/2009

OTHER PUBLICATIONS

International Preliminary Report on Patentability—PCT/US2015/017258.

* cited by examiner

*Primary Examiner* — Jacqueline F Stephens
(74) *Attorney, Agent, or Firm* — J. M. Robertson, LLC

(57) ABSTRACT

A composite loop face fabric which incorporates a multi-bar stitch-bonded construction and related fastening system. A yarn system forms an arrangement of surface loops extending in stitched relation through a composite nonwoven substrate incorporating one or more layers of melt blown nonwoven fibrous material in sandwiched relation to one or more layers of spunbond nonwoven fibrous material. Multiple layers of melt blown nonwoven material and/or spunbond nonwoven material may be used if desired.

20 Claims, 3 Drawing Sheets

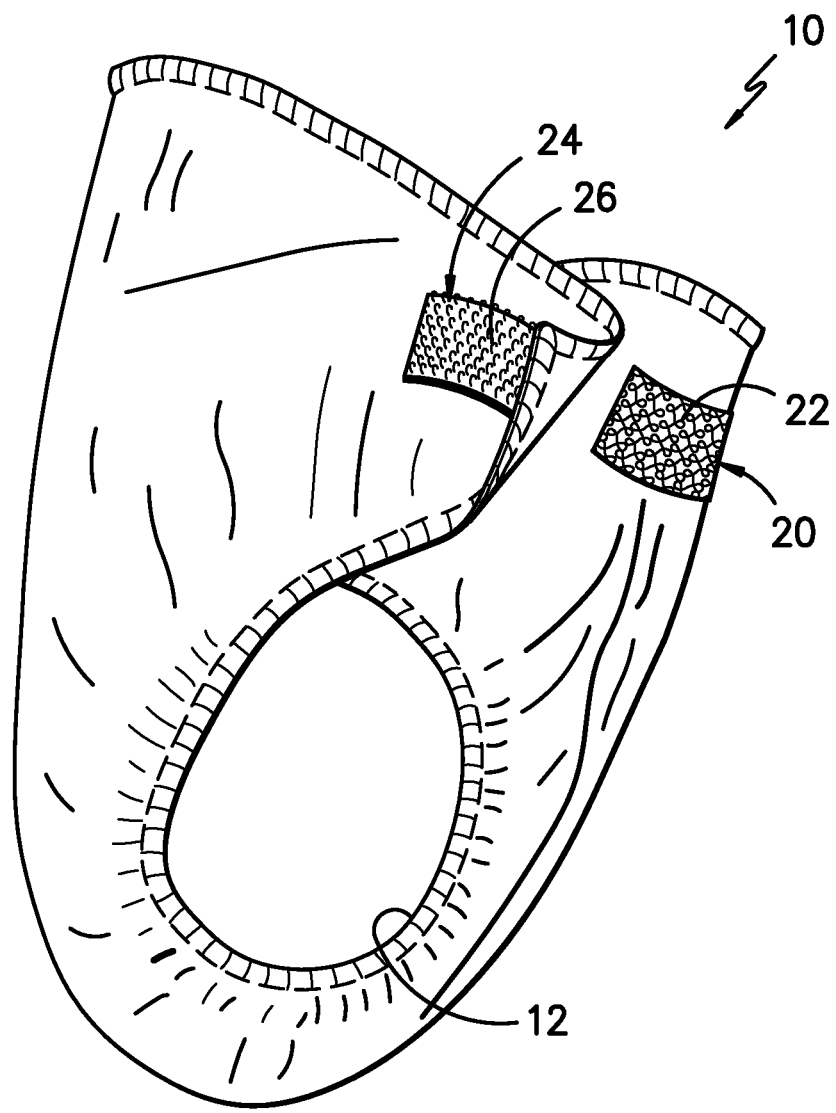
FIG. -1-

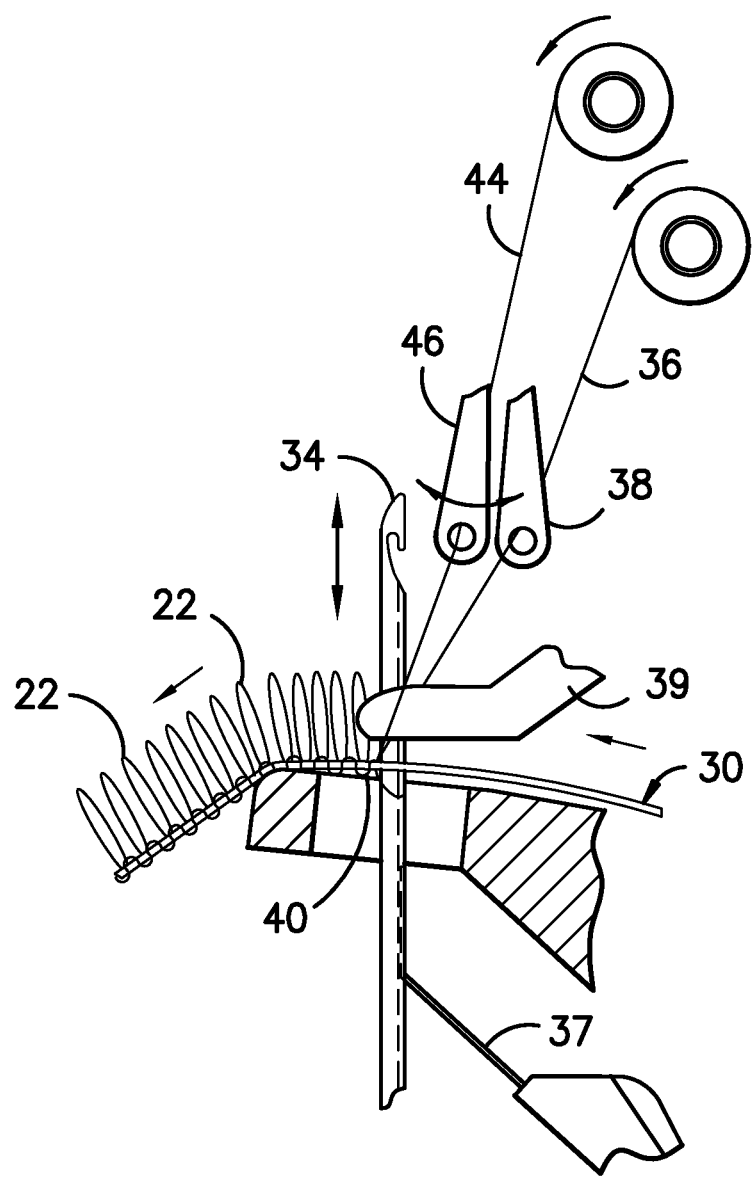
FIG. -2-

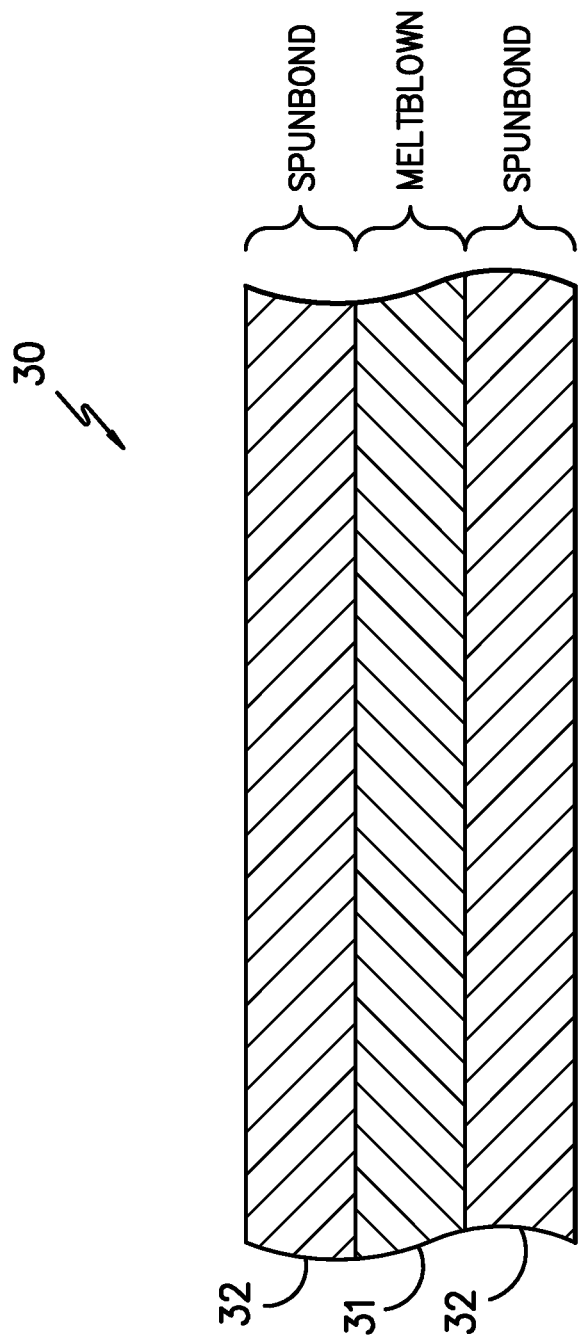

LOOP FASTENER MATERIAL FOR DIAPER AND RELATED METHOD

TECHNICAL FIELD

The present disclosure relates to a hook and loop fastening system, and more particularly, to a hook and loop fastening system incorporating a loop face composite material of stitch bonded construction including an arrangement of spaced surface loops disposed across at least one surface. The loop face composite material includes a yarn system stitched through a nonwoven substrate defining an arrangement of surface loops of yarn extending above the substrate. The loop face composite material is adapted for use as the loop portion of a tear-away fastening system adapted to engage a cooperating hooking surface. The loop face material may find use as a landing zone for a fastening tab in a diaper or other environment of use.

BACKGROUND OF THE DISCLOSURE

Tear away or contact fastening systems are well known. Such systems incorporate two opposing segments of material which are engageable in substantially juxtaposed relation to one another. A male portion of such a contact fastening system typically incorporates a plurality of outwardly projecting hooking structures, while the female portion incorporates a plurality of outwardly projecting loop structures. Upon engagement between the two cooperating portions, the hooking structures engage the opposing loop structures thereby establishing a bond. This bond may be broken by the application of a peeling action between the two opposing portions of material thereby permitting the male and female portions to be progressively disengaged from one another. The engagement may be reactivated by simply bringing the male and female portions back into contacting juxtaposed relation with one another.

Stitch-bonding is a known process in which yarns are stitched through a substrate to form a coordinated web structure. By way of example only, and not limitation, exemplary stitch-bonding processes are disclosed in U.S. Pat. Nos. 6,855,392; 6,869,660; and 7,294,387 all of which are incorporated by reference as if fully set forth herein. In the past, stitch-bonding has been used in the manufacture of loop face composite material to form the loop portion of a tear-away fastening system in a diaper using an LDPE film at the stitching substrate. By way of example only, and not limitation, such materials are disclosed in U.S. Pat. No. 8,632,517 to Wildeman et al., the contents of which are incorporated herein by reference in their entirety.

A benefit of using a film as the stitching substrate in prior loop face composite materials is that even with the piercing of the stitch-forming needles, the resulting stitched composite maintains a low Frasier air permeability of about 25 cubic feet per minute (CFM) when measured according to ASTM D737. Maintaining low air permeability is important in the processing of the stitch-bonded material during diaper production.

According to one exemplary diaper formation practice, a continuous roll of the stitch-bonded material (ranging from about 140 mm-180 mm width) may be fed into a diaper machine and a hot melt adhesive is applied to the non-loop side of the material. The fabric then is cut into a part that the machine then adheres onto the front of the diaper. During this attachment procedure, a vacuum drum or belt is used to control and transport the cut part for assembly onto the diaper. In the event that the stitch-bonded material is too permeable to air flow, the vacuum system may have difficulty in controlling the cut part, and the attachment procedure may be compromised.

While the film substrate provides excellent performance, one potential deficiency of using a film substrate is that some users may prefer a material having a more fabric-like feel. In order to address this preference, attempts have been made to substitute a nonwoven polypropylene spunbonded substrate in place of the film. However, the air permeably of the resulting material was too high to permit reliable use with the vacuum system of the diaper formation machine.

Accordingly a stitch-bonded loop face composite incorporating a nonwoven substrate to impart a fabric feel while maintaining a suitably low air permeability to operate with a diaper machine vacuum system would be of substantial benefit.

SUMMARY OF THE DISCLOSURE

In accordance with one exemplary feature, the present disclosure provides advantages and alternatives over the prior art by providing a composite loop face fabric which incorporates a multi-bar stitch-bonded construction and related fastening system. A yarn system forms an arrangement of surface loops extending in stitched relation through a composite nonwoven substrate incorporating one or more layers of meltblown nonwoven material in sandwiched relation to one or more layers of spunbond nonwoven material. Such substrate materials may be generally referred to as SMS nonwovens, although multiple layers of meltblown nonwoven material and/or spunbond nonwoven may be used if desired. The layers of the substrate may be connected before stitching or may be connected by the stitchbonding procedure. The final stitched composite is characterized by a relatively low air permeability suitable for operation with a diaper machine vacuum system, while eliminating the use of the film substrate.

In one exemplary aspect, the present disclosure provides a diaper having a releasable fastening system. The fastening system includes a fastening tab with a segment of hook material having a plurality of outwardly projecting hooking elements. The fastening system further includes a segment of loop material disposed at a portion of the diaper remote from the fastening tab. The segment of loop material including a plurality of outwardly projecting loop elements is adapted to engage the hooking elements in juxtaposed contacting relation. The loop material comprises a composite sheet of stitch bonded construction including a multi-layer nonwoven substrate with a first plurality of yarn elements extending in stitched relation through the substrate layer to define a ground layer of flat stitches. The composite sheet of stitch bonded construction further includes a second plurality of yarn elements extending in stitched relation through the substrate layer in zigzag crossing relation between parallel needle lines to define said plurality of outwardly projecting loop elements extending above the ground layer of flat stitches. The multi-layer nonwoven substrate comprises at least one layer of a melt blown nonwoven fibrous material disposed in sandwiched relation between covering layers of spunbond nonwoven fibrous material. The loop material may has a weight of not greater than about 45 grams per square meter.

Other exemplary aspects of the disclosure will become apparent upon review of the following detailed description of preferred embodiments and practices.

BRIEF DESCRIPTION OF THE DRAWINGS

The accompanying drawings, which are incorporated in, and which constitute a part of this specification, illustrate exemplary constructions and procedures in accordance with the present disclosure and, together with the general description of the disclosure given above and the detailed description set forth below, serve to explain the principles of the disclosure wherein:

FIG. 1 illustrates a diaper incorporating a fastening arrangement utilizing cooperating hook and loop structures;

FIG. 2 illustrates schematically a two bar stitch-bonding process for selectively forming a surface loop yarn system and a cooperating ground yarn system through a substrate; and FIG. 3 is a schematic cross-sectional view of an exemplary nonwoven stitching substrate.

While exemplary features of the disclosure have been illustrated and are generally described above and will hereinafter be described in connection with certain potentially preferred embodiments and practices, it is to be understood that in no event is the disclosure limited to such illustrated and described embodiments and practices. On the contrary, it is intended that the present disclosure shall extend to all alternatives and modifications as may embrace the general principles of this disclosure within the full and true spirit and scope thereof.

DESCRIPTION OF THE PREFERRED EMBODIMENT(S)

Turning now to the drawings, in FIG. 1 there is illustrated a diaper 10 including a leg opening 12 and a releasable, adjustable fastening assembly. The fastening assembly incorporates a first segment of material 20 including a plurality of outwardly projecting loop elements 22 and a second segment of material 24 incorporating a plurality of outwardly projecting hooking elements 26. By the term "hooking elements" is meant elements having a geometry adapted to releaseably engage the loop elements 22 upon contact. By way of example only, and not limitation, such hooking elements 26 may be configured to have a hooked terminal end and/or an enlarged terminal end such as a "mushroom" shape or the like to become engaged within the loop elements 22. Of course it is to be appreciated that the relative position of the first segment of material 20 incorporating the loop elements 22 and the second segment of material 24 incorporating the hooking elements 26 may be reversed if desired. However, in a diaper, the material forming the loop elements 22 is most typically disposed across a zone overlying a user's abdominal region as shown and will define a landing zone for the hooking elements 22 which are typically disposed across outwardly extending tabs.

It is to be appreciated that the length of one or both of the first and second segments of material 20, 24 may be adjusted so as to provide a desired arrangement for properly adjusting the diaper 10. By way of example only and not limitation, it is contemplated that in the illustrated arrangement wherein the first segment of material 20 incorporating the loop elements 22 is disposed across a forward portion of the diaper 10, such first segment of material 20 may extend across an extended length thereby providing an extended landing zone surface for engagement with the second segment of material 24 during the joining process. This arrangement may facilitate adjustment of the diaper 10 to users of various size.

According to the exemplary practice, the first segment of material 20 is of a so called "stitch bonded" construction having substantially parallel rows of stitches extending through a substrate. Such materials may be formed using a multi-bar stitch bonding apparatus as illustrated schematically in FIG. 2 and the operation of which will be well known to those of skill in the art.

Referring now to FIG. 2, in the illustrated practice, a substrate material 30 of nonwoven construction is conveyed to a stitch-forming position in the direction indicated by the arrow. As will be appreciated by those of skill in the art, the stitch-forming position is defined by a row of reciprocating needles 34, extending in adjacent relation to one another across the width of the substrate material 30 substantially transverse to the direction of movement of the substrate material 30. While only a single needle has been illustrated, in actual practice a large number of such needles are arranged in close relation to one another in the cross-machine direction between the fingers 39 of a sinker bar. It is contemplated that the so-called gauge or needle density in the cross machine direction may be adjusted as desired.

According to the illustrated exemplary practice, two yarns systems (i.e. two bars) are used to form stitches through the substrate material 30. In the illustrated two bar practice, ground yarns 36 forming a first yarn system are carried through a first set of moveable yarn guides 38 manipulated by a back guide bar (not shown) for engagement with needles 34, across the width of the substrate material 30. While only a single ground yarn 36 is illustrated, it will be understood that in practice multiple ground yarns are present across the width of the stitch-forming apparatus. By way of example only, and not limitation, the ground yarns 36 may have a linear density of about 20 denier to about 300 denier. One such suitable yarn for use in a diaper attachment is 40-denier/12 filament fully oriented polyester yarn. However, other yarn constructions and filament counts including monofilament may likewise be utilized if desired. The final stitched weight of the first segment of material 20 is preferably not greater than about 45 grams per square meter, and is more preferably about 15 to 40 grams per square meter. However, higher or lower weights may likewise be used if desired.

According to the potentially preferred practice, the ground yarns 36 are in a fully threaded arrangement to engage each needle. In operation, each ground yarn 36 preferably engages a single needle 34 which moves up and down in a reciprocating manner through the substrate material 30. As will be appreciated by those of skill in the art, in operation, the needle 34 engages a closing wire 37 to close the needle on the downstroke and to reopen it on the upstroke so as to form an arrangement of stitch lines running in the machine direction along the length of the substrate material. As illustrated schematically in FIG. 2, the ground yarns 36 do not cross between needle lines and thus do not pass over the fingers 39 of the sinker bar. According to one desirable practice, the stitch lines formed by the ground yarns 36 are sufficiently close to cover the upper surface of the substrate material 30.

The loop elements 22 may be formed by a loop yarn 44 threaded through moveable yarn guides 46 carried by a front guide bar (not shown). The loop yarn 44 is preferably substantially fully threaded relative to the needles 34. While only a single loop yarn 44 is illustrated for explanatory purposes, it is to be understood that in actual practice, multiple loop yarns 44 are used across the width of the fabric. By way of example only, and not limitation, the loop yarns 44 may have a linear density of about 20 denier to about 300 denier. One such suitable yarn for use in a diaper attachment is a 40 denier/12 filament fully oriented polyester yarn. However, other yarn constructions and filament counts including monofilament may likewise be utilized if desired.

In the fully threaded arrangement, the loop yarns 44 will form a substantially continuous pattern of loop elements 22. The loop elements 22 are formed by passing the loop yarns 44 back and forth in a zigzag pattern between adjacent needles 34 over the fingers 39 of the sinker bar. During the stitch-forming reciprocating action of the needles 34, the fingers 39 of the sinker bar hold the crossing segments of the loop yarns above the substrate, thereby yielding upstanding loops rather than flat stitches. By way of example only, a pile sinker height of about 2 mm may be used. However, other heights may be used if desired.

In accordance with one exemplary practice, the substrate material 30 is a so called "SMS" nonwoven. As shown in FIG. 3, the exemplary substrate material 30 includes one or more interior layers of a melt blown nonwoven fibrous material 31 formed from a suitable polymer such as polypropylene, polyester (PET), polyamide or the like disposed in sandwiched relation to one or more covering layers of spunbond nonwoven fibrous material 32 formed from a suitable polymer such as polypropylene, polyester (PET), polyamide or the like. In this regard, the construction illustrated in FIG. 3 is an SMS construction with a single layer of meltblown nonwoven fibrous material 31 sandwiched between two opposing layers of spunbond nonwoven fibrous material 32. However, it is likewise contemplated that multiple layers of meltblown nonwoven fibrous material 31 may be used to form structures such as SMMS, SMMMS, SMMMMS, and so forth. It is also contemplated that multiple layers of spunbond nonwoven fibrous material 32 may be used on either side if desired to form structures such as SSMSS, SSMMSS, SSMMMSS, SSMMMMSS, SSSMSSS, SSSMMSSS, SSSMMMSSS, SSSMMMMSSS and the like. Of course, such laminate arrangements are exemplary only and it is contemplated that sandwich structures having any number of layers of each material may be used as may be desired. Thus, each of the layers marked in FIG. 3 may be made up of a single layer or multiple layers of the designated material. By way of example only, an adhesive bond may be present between the layers due to melt adhesion between layers and/or by use of supplemental adhesives at the layer interfaces.

While FIG. 2 illustrates a single layer of substrate material being delivered to a stitch-forming position, it is likewise contemplated that two or more webs of multi-layered substrate material 30 as described above may be delivered concurrently in stacked relation to one another. In the event that two or more webs of the substrate material are used, they may each have either the same layered relation or they may have different layered relations. By way of example only, in the event that two webs of substrate material 30 are used, each layer may have an SMS construction, or one layer may have an SMS construction, while the other layer has an SMMMS or other construction. Of course, three or more layers may be used if desired, and substantially any combination of layer constructions may be used as may be desired. It is contemplated that the use of multiple lightweight webs may be beneficial in providing a lower air permeability and higher strength after stitching without the need to use a substantial mass of fibrous material.

It is also contemplated that the individual layers forming the SMS or other substrate material 30 may be delivered to the stitching location as separate layers without being prebonded to the other layers. In such a practice, the stitching then may provide the bonding relation between the layers without adhesive bonding. Of course, combinations of any of the described practices may be used if desired.

As will be appreciated by those of skill in the art, the meltblown nonwoven 31 is typically very weak and would not normally be considered suitable as a substrate material 30 in a stitch bonding procedure. However, the spunbond components have been found to provide adequate strength and resistance to tearing after stitching. Surprisingly, it has also been found that a combination of spunbond and meltblown components also may provide a relatively low air permeability at low weights so as to be suitable for use with a diaper machine vacuum system.

COMPARATIVE EXAMPLES

The disclosure may be further understood through reference to the following non-limiting examples.

In the examples reported in TABLE 1 below, loop face stitch bonded fabrics were produced using corresponding manufacturing procedures but with different substrates. Air permeability was measured using a Frasier Air Permeability test unit according to ASTM standard D737 with a Differential Water Pressure (DWP) of 0.5 inches. The rate of air flow across the sample produced by the differential pressure is measured. Specifically, a circle of fabric is clamped into the tester and through the use of a vaccum, the air pressure is made different on one side of the fabric. Airflow will occur from the side with higher air pressure, through the fabric, to the side with the lower air pressure. From this rate of air flow, the air permeability of the fabric is determined.

Permeability is expressed in units of cubic feet per minute (CFM) on the basis of one square foot of fabric. As may be seen, while the LDPE film substrate provided the lowest air permeability, it also exhibited the highest stitched weight. Conversely, using a single layer of spunbond polypropylene resulted in a low weight product, but also produced undesirably high air permeability. Substrates incorporating a simple SMS construction with a layer of meltblown polypropylene between layers of spunbond polypropylene produced light weight fabrics while maintaining relatively low air permeability levels which are believed to be suitable for use with diaper forming vacuum machinery. In particular, the exemplary constructions exhibit air permeability levels of less than 300 CFM per square foot and more preferably less than 200 CFM per square foot when tested according to ASTM standard D737. The materials and practices of the present disclosure thus provide a significant and desirable advancement over the prior art.

TABLE 1

AIR PERMEABILITY TESTING PERFORMANCE OF 2 BAR STITCHBONDED LOOP FASTENER MATERIALS WITH DIFFERENT SUBSTRATES

| Substrate Material Type | Substrate Material Comp. | Substrate Weight (g/m$^2$) | Stitched Weight (g/m$^2$) | Substrate ONLY Air Perm. CFM/ft$^2$ | Stitched Substrate Air Perm. CFM/ft$^2$ |
|---|---|---|---|---|---|
| Film | LDPE | 33.0 | 40.0 | 0 | 25 |
| Spunbond | Polyprop. | 15.0 | 21.5 | 796 | 591 |
| SMS | Polyprop. | 15.0 | 21.5 | 223 | 277 |
| SMS | Polyprop. | 20.0 | 26.5 | 205 | 243 |
| SMS | Polyprop. | 30.0 | 37.0 | 142 | 157 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A diaper having a releasable fastening system, the fastening system comprising:
   a fastening tab including a segment of hook material having a plurality of outwardly projecting hooking elements; and
   a segment of loop material disposed at a portion of the diaper remote from the fastening tab, the segment of loop material including a plurality of outwardly projecting loop elements adapted to engage the hooking elements in juxtaposed contacting relation, wherein the loop material comprises a composite sheet of stitch bonded construction including a multi-layer nonwoven substrate with a first plurality of yarn elements extending in stitched relation through the substrate layer to define a ground layer of flat stitches, and wherein the composite sheet of stitch bonded construction further includes a second plurality of yarn elements extending in stitched relation through the substrate layer in zigzag crossing relation between parallel needle lines to define said plurality of outwardly projecting loop elements extending above the ground layer of flat stitches, wherein the multi-layer nonwoven substrate comprises at least one layer of a melt blown nonwoven fibrous material disposed in sandwiched relation between covering layers of spunbond nonwoven fibrous material, and wherein the loop material has a weight of not greater than about 45 grams per square meter.

2. The diaper as recited in claim 1, wherein the segment of loop material is disposed at a position on the diaper overlying a user's abdominal region.

3. The diaper as recited in claim 2, wherein the first plurality of yarn elements extends in stitched relation through the substrate layer to define a plurality of parallel stitch lines of flat stitches extending along the machine direction of the sheet material.

4. The diaper as recited in claim 3, wherein the parallel stitch lines of flat stitches cooperatively form a ground layer substantially covering an upper surface of the substrate layer.

5. The diaper as recited in claim 1, wherein the loop material is characterized by a Frasier air permeability of not greater than about 300 CFM per square foot at a differential water pressure of 0.5 inches of water when tested according to ASTM test method D737.

6. The diaper as recited in claim 1, wherein the loop material is characterized by a Frasier air permeability of not greater than about 250 CFM per square foot at a differential water pressure of 0.5 inches of water when tested according to ASTM test method D737.

7. The diaper as recited in claim 6, wherein the loop material has a weight of less than 40 grams per square meter and wherein said at least one layer of a melt blown nonwoven fibrous material comprises polypropylene and said covering layers of spunbond nonwoven fibrous material each comprise polypropylene.

8. The diaper as recited in claim 6, wherein the loop material has a weight of less than 30 grams per square meter and wherein said at least one layer of a melt blown nonwoven fibrous material comprises polypropylene and said covering layers of spunbond nonwoven fibrous material each comprise polypropylene.

9. The diaper as recited in claim 1, wherein the loop material is characterized by a Frasier air permeability of not greater than about 200 CFM per square foot at a differential water pressure of 0.5 inches of water when tested according to ASTM test method D737.

10. The diaper as recited in claim 9, wherein the loop material has a weight of less than 40 grams per square meter and wherein said at least one layer of a melt blown nonwoven fibrous material comprises polypropylene and said covering layers of spunbond nonwoven fibrous material each comprise polypropylene.

11. The diaper as recited in claim 1, wherein the loop material is characterized by a Frasier air permeability of not greater than about 175 CFM per square foot at a differential water pressure of 0.5 inches of water when tested according to ASTM test method D737.

12. The diaper as recited in claim 11, wherein the loop material has a weight of less than 40 grams per square meter and wherein said at least one layer of a melt blown nonwoven fibrous material comprises polypropylene and said covering layers of spunbond nonwoven fibrous material each comprise polypropylene.

13. The diaper as recited in claim 1, wherein the loop material is characterized by a Frasier air permeability of not greater than about 160 CFM per square foot at a differential water pressure of 0.5 inches of water when tested according to ASTM test method D737.

14. The diaper as recited in claim 13, wherein the loop material has a weight of less than 40 grams per square meter and wherein said at least one layer of a melt blown nonwoven fibrous material comprises polypropylene and said covering layers of spunbond nonwoven fibrous material each comprise polypropylene.

15. The diaper as recited in claim 13, wherein said at least one layer of a melt blown nonwoven fibrous material is secured to said covering layers of spunbond nonwoven fibrous material by said first plurality of yarn elements without adhesive bonding.

16. The diaper as recited in claim 1, wherein said at least one layer of a melt blown nonwoven fibrous material is adhesively bonded to said covering layers of spunbond nonwoven fibrous material.

17. A diaper having a releasable fastening system, the fastening system comprising:
  a fastening tab including a segment of hook material having a plurality of outwardly projecting hooking elements; and
  a segment of loop material disposed at a portion of the diaper remote from the fastening tab, the segment of loop material including a plurality of outwardly projecting loop elements adapted to engage the hooking elements in juxtaposed contacting relation, wherein the loop material comprises a composite sheet of stitch bonded construction including a multi-layer nonwoven substrate with a first plurality of yarn elements extending in stitched relation through the substrate layer to define a ground layer of flat stitches substantially covering an upper surface of the substrate layer, and wherein the composite sheet of stitch bonded construction further includes a second plurality of yarn elements extending in stitched relation through the substrate layer in zigzag crossing relation between parallel needle lines to define said plurality of outwardly projecting loop elements extending above the ground layer, wherein the multi-layer nonwoven substrate comprises at least one layer of a melt blown nonwoven polypropylene fibrous material disposed in sandwiched relation between covering layers of spunbond nonwoven polypropylene fibrous material, and wherein the loop material is characterized by a Frasier air permeability of not greater than about 300 CFM per square foot at a differential water pressure of 0.5 inches of water when tested according to ASTM test method D737 and wherein the loop material has a weight of not greater than about 40 grams per square meter.

18. The diaper as recited in claim 17, wherein the loop material is characterized by a Frasier air permeability of not greater than about 200 CFM per square foot at a differential water pressure of 0.5 inches of water when tested according to ASTM test method D737.

19. The diaper as recited in claim 17, wherein the loop material is characterized by a Frasier air permeability of not greater than about 175 CFM per square foot at a differential water pressure of 0.5 inches of water when tested according to ASTM test method D737.

20. The diaper as recited in claim 17, wherein the loop material is characterized by a Frasier air permeability of not greater than about 160 CFM per square foot at a differential water pressure of 0.5 inches of water when tested according to ASTM test method D737.

* * * * *